United States Patent
Chotenovsky et al.

(10) Patent No.: US 9,622,750 B2
(45) Date of Patent: Apr. 18, 2017

(54) ELASTIC BAND LIGATION DEVICE WITH LOCKING MECHANISM AND METHOD FOR TREATMENT OF HEMORRHOIDS

(71) Applicant: CRH MEDICAL CORPORATION, Vancouver (CA)

(72) Inventors: David Chotenovsky, Barrie (CA); Mitchel Guttenplan, Roswell, GA (US)

(73) Assignee: CRH MEDICAL CORPORATION, Vancouver, BC (CA)

( * ) Notice: Subject to any disclaimer, the term of this patent is extended or adjusted under 35 U.S.C. 154(b) by 147 days.

(21) Appl. No.: 13/972,168

(22) Filed: Aug. 21, 2013

(65) Prior Publication Data
US 2015/0057679 A1 Feb. 26, 2015

(51) Int. Cl.
*A61B 17/12* (2006.01)
*A61B 17/00* (2006.01)

(52) U.S. Cl.
CPC ............... *A61B 17/12009* (2013.01); *A61B 2017/00818* (2013.01); *A61B 2017/12018* (2013.01)

(58) Field of Classification Search
CPC ........ A61B 17/12013; A61B 17/12009; A61B 17/12; A61B 2017/12018; A61B 2017/306; A61B 2017/347; A61B 2017/00296; A61B 2017/12004; A61F 5/0089; A61F 6/20; A61F 6/18; A61F 2002/9517; A61M 2025/0006; A61M 2025/0293; A61M 25/0119; A61M 25/0625

(Continued)

(56) References Cited

U.S. PATENT DOCUMENTS 5,361,461 A * 11/1994 Anscher .................... 24/115 G
5,741,273 A    4/1998 O'Regan
(Continued)

FOREIGN PATENT DOCUMENTS

JP    2005-110983 A    4/2005
JP    2009-183460 A    8/2009
(Continued)

OTHER PUBLICATIONS

PCT Notification of Transmittal of the International Search Report and Written Opinion mailed May 21, 2014, PCT International Application No. PCT/US2013/066390, International filing date Oct. 23, 2013 (14 pgs).
PCT Notification of Transmittal of the International Search Report and Written Opinion mailed May 21, 2014, PCT International Application No. PCT/US2013/066397, International filing date Oct. 23, 2013 (11 pgs).

(Continued)

*Primary Examiner* — Darwin Erezo
*Assistant Examiner* — Katherine Schwiker
(74) *Attorney, Agent, or Firm* — Nixon & Vanderhye P.C.

(57) ABSTRACT

Elastic band ligation device for treating hemorrhoidal tissue, including an inner tube for retaining an elastic band, a plunger in the inner tube for drawing hemorrhoidal tissue into the inner tube, and an outer tube pusher sleeve disposed over the inner tube. A thumb pusher on the sleeve allows the operator to push the sleeve towards the front of the inner tube to deploy the elastic band from the front end of the inner tube onto hemorrhoidal tissue drawn into the inner tube. The sleeve has a locking mechanism including a tab for locking the sleeve to the inner tube to prevent relative movement of the sleeve and inner tube until the sleeve is unlocked by the user, thereby preventing premature deployment of an elastic band.

15 Claims, 8 Drawing Sheets

(58) Field of Classification Search
USPC ............... 606/140–142; 604/164.01, 164.09, 604/165.01, 271; 600/184
See application file for complete search history.

(56) References Cited

U.S. PATENT DOCUMENTS

| | | |
|---|---|---|
| 7,488,333 B2 | 2/2009 | Ghareeb |
| 2002/0072757 A1 | 6/2002 | Ahmed et al. |
| 2003/0199915 A1* | 10/2003 | Shimm ............... A61B 17/3439 606/198 |
| 2004/0267287 A1* | 12/2004 | Nesper et al. ................ 606/148 |
| 2005/0107816 A1* | 5/2005 | Pingleton et al. ............ 606/185 |
| 2007/0123971 A1* | 5/2007 | Kennedy, II ............... A61F 2/95 623/1.11 |
| 2009/0198255 A1* | 8/2009 | Ikeda ............... A61B 17/12013 606/140 |
| 2010/0063517 A1 | 3/2010 | Cleator |

FOREIGN PATENT DOCUMENTS

| | | | |
|---|---|---|---|
| WO | WO 94/08517 A1 | | 4/1994 |
| WO | WO 00/03642 | * | 1/2000 |

OTHER PUBLICATIONS

PCT Notification of Transmittal of the International Search Report and Written Opinion mailed May 1, 2014, PCT International Application No. PCT/US2013/066407, International filing date Oct. 23, 2013 (12 pgs).

* cited by examiner

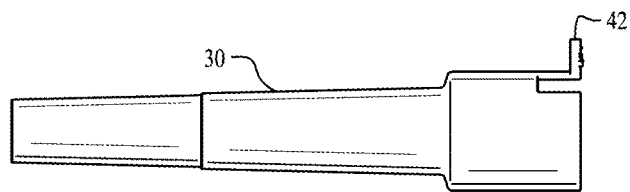
FIG. 3B
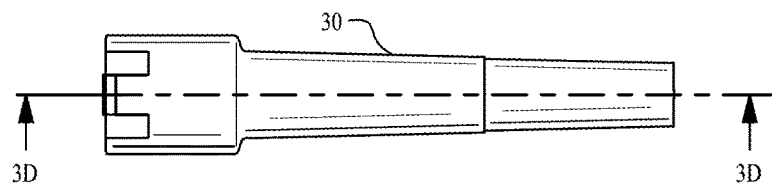
FIG. 3C
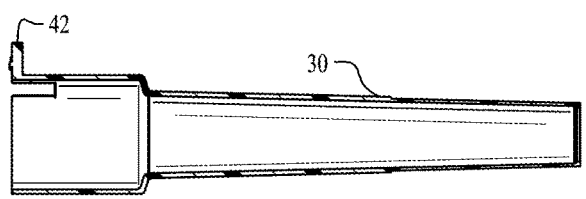
FIG. 3D
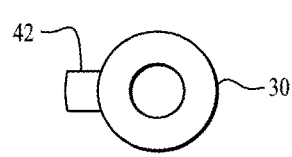 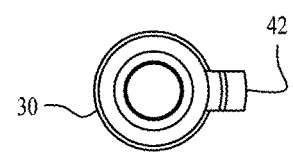
FIG. 3E FIG. 3F
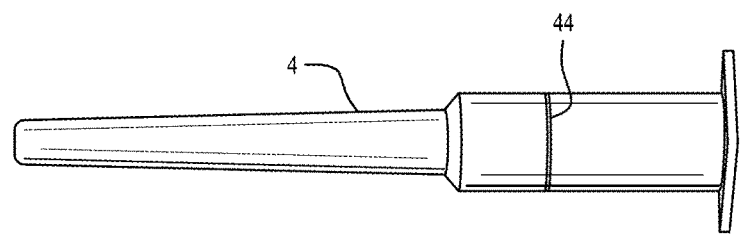
FIG. 4

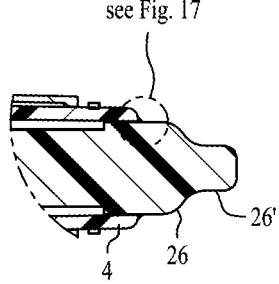
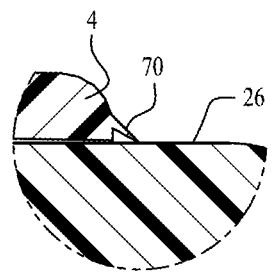
FIG. 16          FIG. 17
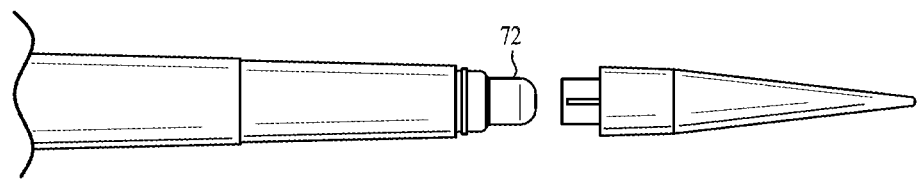
FIG. 18
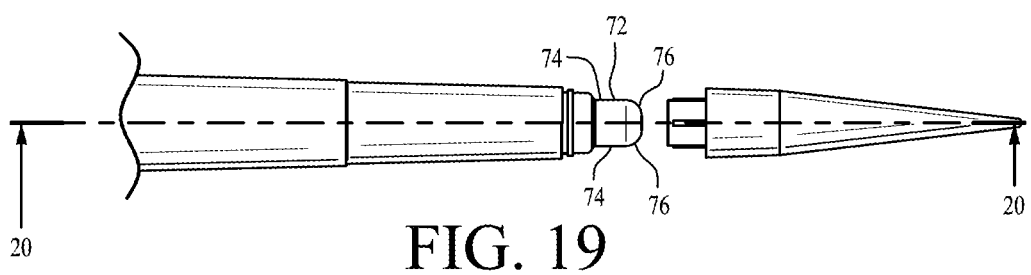
FIG. 19
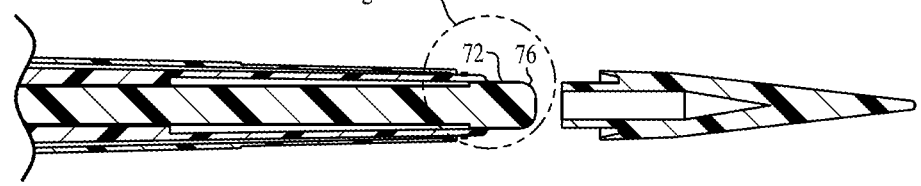
FIG. 20

ELASTIC BAND LIGATION DEVICE WITH LOCKING MECHANISM AND METHOD FOR TREATMENT OF HEMORRHOIDS

BACKGROUND OF THE INVENTION

The present invention relates to the treatment of hemorrhoids by elastic band ligation. More specifically the invention relates to an elastic band ligation device that is provided with a locking mechanism which prevents premature elastic band deployment.

Commonly assigned patent applications entitled ELASTIC BAND LIGATION DEVICE WITH ITEGRATED OBTURATOR AND METHOD FOR TREATMENT OF HEMORRHOIDS (U.S. application Ser. No. 13/972,144) and ELASTIC BAND LIGATION DEVICE WITH ANTI-PINCH FEATURE AND METHOD FOR TREATMENT OF HEMORRHOIDS (U.S. application Ser. No. 13/972, 202) are filed simultaneously herewith, the entire disclosures of which are hereby incorporated by reference herewith.

Treatment of hemorrhoids by elastic band ligation typically involves placing an elastic band on hemorrhoidal tissue in the rectum well above the "dentate line" (the junction of the sensitive squamous epithelium known as the "anoderm" and the insensitive lining of the rectum known as the "mucosa"), where there is little sensation. The tissue trapped in the band is cut off from its blood supply, degenerates and is sloughed, and the elastic band along with the sloughed tissue is passed with bowel motions. More importantly, however, the resulting healing process causes the tissue in the vicinity to become fixed, and prolapse of the hemorrhoidal tissue is minimized. This fixation of the tissue serves to eliminate the hemorrhoidal symptoms.

Many devices exist on the market utilizing the elastic band ligation technique. Examples are U.S. Pat. No. 5,203, 863 to Bidoia, U.S. Pat. No. 5,122,149 to Broome, U.S. Pat. No. 5,158,563 to Cosman and U.S. Pat. No. 5,741,273 to O'Regan. The devices disclosed in U.S. Pat. No. 5,203,863 to Bidoia, U.S. Pat. No. 5,122,149 to Broome, U.S. Pat. No. 5,158,563 to Cosman are generally designed to be used in conjunction with an instrument such as a proctoscope or anoscope to directly see the area to be banded. In some cases, it is necessary to employ an assistant to hold the proctoscope or anoscope. However, the use of these scopes, which are generally larger in diameter than banding apparatus, can cause considerable discomfort to a patient and more specifically to one who is suffering symptoms of hemorrhoids and other associated issues.

The device disclosed in U.S. Pat. No. 5,741,273 to O'Regan relates to an elastic band ligation device for treatment of hemorrhoids that may be used without directly seeing the site for banding. Thus, it may be used without a proctoscope or anoscope or any other type of scope or viewing technique. Therefore, because the device can be inserted into the rectum and positioned appropriately without simultaneous visualization, or the need for any type of scope, the banding procedure performed in this manner causes less discomfort to the patient. This technique also allows for a more proximal placement of the elastic band, which increases the technique's efficacy as well as causing less discomfort and fewer complications. This device has a suction device incorporated therein to draw hemorrhoidal tissue into an aperture for banding without requiring a second operator or connection to an aspirator.

Ligation is typically performed by initially inspecting the site through a small scope such as a sigmoidoscope, anoscope, proctoscope or other type of scope and making a mental note as to the area where the band should optimally be placed. The scope is then removed and the ligation device is placed in the rectum. This is known as the "Blind" or "Touch" technique.

An alternative application is to visualize the area with an anoscope and insert the banding through the lumen of the anoscope and band directly. This can be done if the operator prefers a direct visual approach. This is known as the "Trans-anoscopic" or "visual" technique.

The front end of the device is inserted well past the site for banding. Then, the device is gently withdrawn while it is pointed in the direction of the anal canal, minimizing patient discomfort. As the device is being withdrawn, a palpable "ridge" on the outside of the outer tubular member is noted at the anal verge which can be used as a guide to the level where the band should optimally be placed in the rectum. The device is then gently angled or "aimed" toward the hemorrhoid to be treated. In larger patients, the operator may choose to place the device 1-2 cm further in through the anus prior to "aiming" the device towards the hemorrhoid to be treated.

However, it has been found that prior devices suffer from the drawback that the elastic band(s) may undergo premature deployment, with the result that it is necessary to withdraw the device, recover the deployed elastic band within the rectum and begin the procedure again. This gives rise to delays and additional discomfort to the patient. From a patient and physician perspective, a quick smooth banding is most desirable. One situation that can prolong the treatment process is if the band is deployed at the incorrect moment, leading to the need to re-load the band on the device. If this occurs when the device is inserted in the patient, the discomfort to the patient is increased.

Currently the main cause for pre-mature band deployment is that the pusher (that pushes the band off the body of the ligator) can move freely on its own as it is held with minimal frictional force on the device. If the pusher moves for whatever reason, the band can be deployed at the incorrect moment. A need exists therefore for a mechanism that would give the physician control over timing as to when the band is deployed. The general function of the device would remain the same, thereby permitting training for existing users to be relatively quick. The present invention seeks to satisfy that need.

BRIEF DESCRIPTION OF THE INVENTION

The present invention provides an elastic band ligation device for treatment of hemorrhoidal tissue comprising an inner tubular member having a front end and a rear end, for retaining a stretched elastic band over the front end thereof, the front end having an opening, a plunger in the tubular member with a handle extending away from the front end of the inner tubular member, the handle for sliding the plunger away from the front end of the inner tubular member to provide a suction for drawing hemorrhoidal tissue into the inner tubular member through the opening at the front end, an outer tubular pusher sleeve configured to provide a limited friction fit over the inner tubular member, with an external end of the outer tubular pusher sleeve adjacent the stretched elastic band, and having an opposite end of the outer tubular pusher sleeve provided with thumb push means for an operator to push the outer tubular pusher sleeve towards the front end of the inner tubular member and release the elastic band from the front end of the inner tubular member to engage hemorrhoidal tissue extending through the opening in the inner tubular member, and an outer tubular pusher sleeve locking mechanism including a manually actuated tab connected to the outer tubular pusher sleeve for locking the outer tubular pusher sleeve to the inner sleeve to prevent relative movement of the outer sleeve and inner tubular member until the outer pusher sleeve is unlocked by the user, thereby preventing premature deployment of an elastic band.

In another embodiment, the device may include an anti-pinch feature which reduces the risk of the patient's tissue being trapped as the obturator is retracted into the device.

In a further embodiment, the ligation device is made of plastic and is disposable. Thus, once it has been used it is discarded and does not have to be sterilized. In another embodiment, the ligation device is made of metal and may be sterilized after each use.

The disposable elastic band ligation device of the invention may be used in a doctor's office and does not generally require the administration to the patient of any form of anesthetic. One to three elastic bands are generally placed at each patient visit and as many as six bands may be required in total, particularly in advanced cases.

An obturator may be provided within the inner tubular member and may be connected to the plunger. The obturator is typically integrally formed with the plunger a single unit. The obturator is provided with a rounded smooth end which may be induced to protrude beyond the front end of the inner tubular member by movement of the plunger. The purpose of the obturator is to facilitate access of the ligation device into the rectum of the patient with reduced discomfort to the patient, with minimal training of the physician, and with no requirement for the use of additional piece(s) of equipment.

In another embodiment, the ligation device of the invention may be provided with a separable elastic band introducer device which facilitates introduction of the elastic band(s) onto the front end of the device. In one embodiment, the band introducer is in the general shape of a cone and comprises a front tapered section, a rear section dimensioned such that it can be connected to the front end of the inner tubular member, and a center section disposed between the front and rear sections having an external dimension corresponding to that of the front end of the inner tubular member. The band introducer may be provided with surface channels extending longitudinally to permit insertion of a finger(s) of the user below the band(s) to manipulate the band(s) onto and/or off of the introducer. In use, the rear end of the introducer is connected to the front end of the inner tubular member and an elastic band(s) is (are) rolled over the tapered front section and over the central section onto the front end of the inner tubular member. Once the band(s) has been placed on the front end of the inner tubular member, the introducer is removed prior to use of the ligation device.

An additional feature is the use, in the plastic version of the ligation device, of a plastic retention fixed ring on the inside of the proximal end of the inner tubular member for preventing the plunger from being withdrawn from the inner tubular member and thus preventing the possibility of the instrument being cleaned and reused. Reuse of the device may be possible when the ligator is fabricated from metal, such as stainless steel, which can be sterilized between uses.

A further feature, again in connection with the plastic version of the ligation device, is the use of a treated slightly roughened inside plastic or a material such as Plexiglas SL7 on the inside of the inner tubular member which turns opaque after attempted cleaning and, thus, provides a visual guide that the ligator has been used in one patient and should not be reused.

A yet further feature of the invention resides in a method of treating hemorrhoidal tissue in a patient in need of such treatment. The method comprises the steps of: (a) providing an elastic band ligation device of the invention; b) applying at least one elastic band over the front end of the inner tubular member; (c) inserting the device carrying one elastic band into the rectum of a patient; (d) adjusting the position of the device to arrange the opening at the end of the device to be in direct alignment with the hemorrhoidal tissue; (e) withdrawing the plunger to exert suction on the hemorrhoidal tissue and draw it through the opening into the inner tubular member; and (f) pushing the outer tubular pusher sleeve to engage the outer tubular pusher sleeve against the elastic band to urge the elastic band onto the hemorrhoidal tissue; locking the plunger in place and allowing the engaged ligator to sit in order to allow for more tissue to move inside the inner tubular member; and (g) the option of pushing the outer tubular pusher sleeve to engage the outer tubular pusher sleeve against the elastic band, or to secure the outer tubular pusher sleeve while gently withdrawing the inner tubular member which also engages the outer tubular pusher sleeve against the elastic band in order to urge the elastic band onto the hemorrhoidal tissue.

The device will typically be supplied to end users in the band loading position, that is with the plunger (and obturator if present) pulled back to allow the user to attach the band loading cone, push band(s) over and onto the main body of the ligator and remove the band loading cone. Prior to insertion, the plunger is completely depressed, exposing the smooth, rounded end of the obturator, which will help in the comfortable passage of the ligator into the anorectum. Following insertion of the device into the anus of the patient, the plunger is pulled back to the "ready to draw material" position, which will be the same location as the band loading position and will be marked by: a slight bump/feel in the plunger as in rides over a small detent/ring and/or a mark on the plunger that will align with the end of the ligator or a line or mark on the ligator, and/or texture/color change that will denote visually or by feel that the correct location has been reached. Tissue to be banded is located, and the plunger is pulled back to draw tissue into the inner tubular member until the inner ring is engaged. The device is oscillated 90 to 180 degrees in either direction to ensure tissue is captured properly. The band is deployed by either pushing the pusher forward or by securing the pusher and withdrawing the inner tubular member until the band is deployed. The entire device is then withdrawn.

The term "a limited friction fit" as used herein means that the outer tubular pusher sleeve exerts sufficient friction against the inner tubular member such that the two components do not freely slide with respect to each other but require gentle hand-applied pressure to move one relative to the other.

In one embodiment, the ligation device is made of plastic and is disposable. Thus, once it has been used it is discarded and does not have to be sterilized. In another embodiment, the ligation device is made of metal and may be sterilized after each use.

The disposable elastic band ligation device of the invention may be used in a doctor's office and does not generally require the administration to the patient of any form of anesthetic. One to three elastic bands are generally placed at each patient visit and as many as six bands may be required in total, particularly in advanced cases.

In a further embodiment, the ligation device may be provided with an obturator within the inner tubular member. The obturator may or may not be physically connected to the plunger. The obturator is provided with a rounded smooth end which may be induced to protrude beyond the front end of the inner tubular member by movement of the plunger. The purpose of the obturator is to facilitate access of the ligation device when inserted into the rectum of the patient.

An additional aspect of the invention provides a non-latex elastic band for use in the treatment of patients who exhibit or may exhibit a latex allergic reaction.

BRIEF DESCRIPTION OF THE DRAWINGS

FIG. 3B is a side view of the outer pusher sleeve;

FIG. 3C is a top view of the outer pusher sleeve;

FIG. 3D is a cross-sectional view of the outer pusher sleeve along the line 3D-3D in FIG. 3C;

FIG. 3E is a view from the distal end of the outer pusher sleeve;

FIG. 3F is a view from the proximal end of the outer pusher sleeve;

FIG. 4 is side view of the inner tubular member showing a locking ring on the outer circumference thereof;

FIG. 16 is a cross-sectional view of the circled portion of FIG. 15;

FIG. 17 is a cross-sectional view of the circled portion of FIG. 16;

FIGS. 18 and 19 are side views of another embodiment showing a differently shaped end for the obturator;

FIG. 20 is a cross-sectional view along line 20-20 of FIG. 19;

DETAILED DESCRIPTION OF THE INVENTION

Figure 1:
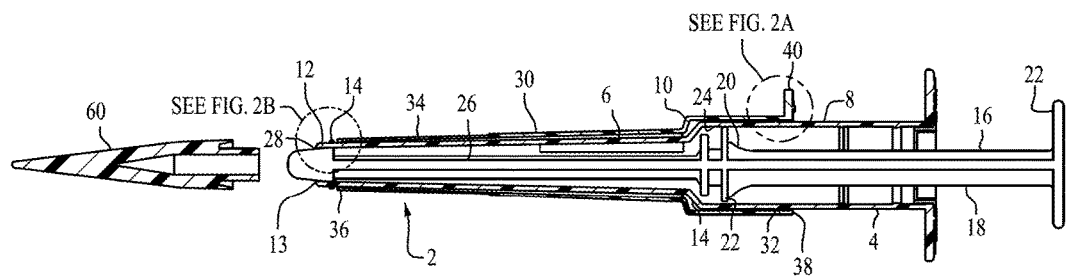
FIG. 1 is a side cross-sectional view of a first embodiment of ligation device of the present invention.

Referring to the drawings, FIG. 1 shows a first embodiment of a ligation device of the invention, generally referenced 2, comprising a plastic inner tubular member 4 having a convergent tubular section 6 with an inner surface 9 and an integrally formed straight cylindrical section 8. The convergent tubular section 6 has a rear end 10 and a front end 12 for retaining a stretched elastic band 14 over the front end 12 thereof.

In the embodiment illustrated in FIG. 1, the inner tubular member 4 has a convergent tubular configuration extending continuously from the rear end 10 to the front end 12 and for a sufficient distance to facilitate insertion into the rectum of a patient.

A plunger 16 is slideably disposed in the cylindrical section 8, and has a stem center section 18, a head 20 at one end of a stem section 18 and a handle 22 at the other end of the stem section 18 and extending away from the front end 12 of the inner tubular member 4. The head 20 is typically fabricated from rubber and is adapted for sealingly engaging with an inner wall of the cylindrical section 8. In the embodiment shown in FIG. 1, a sealing member 23 is mounted on the head 20 for sealingly engaging with the inner wall 24 of the cylindrical section 8.

Figure 8:
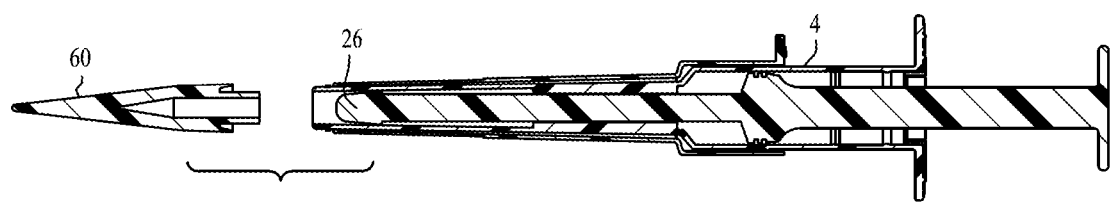
FIG. 8 is a cross-sectional view of the device showing the obturator partially withdrawn inside the device.
Figure 9:
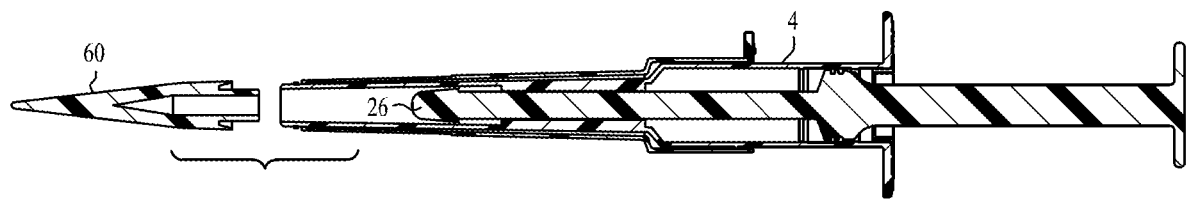
FIG. 9 is a cross-sectional view of the device showing the obturator fully withdrawn inside the device.

In the embodiment shown in FIG. 1, the plunger 16 is integrally formed with an obturator 26 disposed internally of the inner tubular member. The obturator is provided with a rounded end portion 28 which by movement of the plunger may protrude beyond the end 12 of the inner tubular member, through opening 13, as shown in FIG. 1, or may be positioned within the interior of the inner tubular member, as shown in FIGS. 8 and 9 (discussed below). The purpose of the obturator is to facilitate access of the ligation device when inserted into the rectum of a patient.

The handle 22 permits the plunger 16 to be slid away from the front end 12 of the inner tubular member 4 to provide a suction for drawing hemorrhoidal tissue into the inner tubular member 4 through the opening 13 at the front end 12. The opening 13 may be slightly smaller in diameter than the inner tubular member 4. In another embodiment, the cylindrical section 8 and inner tubular member 4 may be separate components joined together.

A plastic outer tubular pusher sleeve 30 is provided and a straight cylindrical section 32 and a tapering tubular section 34 corresponding to the taper of the convergent section of the inner tubular member 4. The outer tubular pusher sleeve 30 has a limited friction fit over the length of the inner tubular member 4, and has an external end 36 adjacent the stretched elastic band 14 and an opposite end 38 provided with a locking mechanism 40.

Figure 2A:
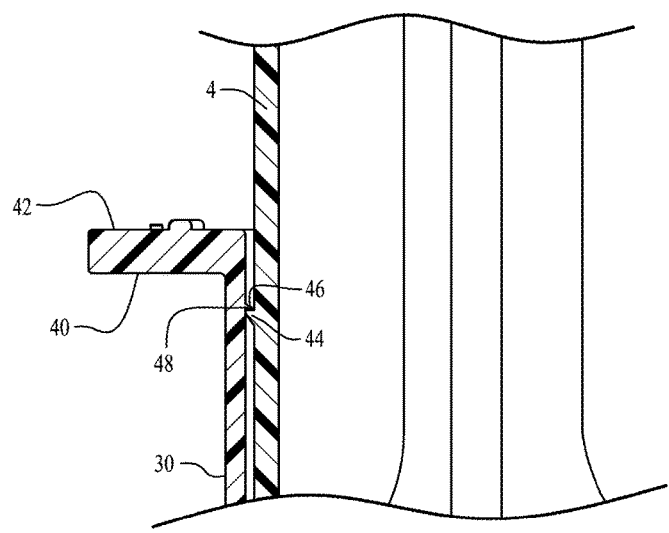
FIG. 2A is an enlarged side view of the of the outer pusher sleeve locking mechanism.

The locking mechanism shown in FIG. 2A and generally referenced 40 includes a tab 42 engageable with a locking ring 44 provided on the exterior surface of the inner tubular member 4. The locking ring has an abutment surface 48 extending at 90 degrees to the outer surface of the inner tubular member. The tab 42 is provided with a lug 46 which protrudes at 90 degrees from the tab 42 and abuts against the abutment surface 48, thereby preventing movement of the outer pusher sleeve towards the front end of the device. Upon pushing the tab 42 away from the inner tubular member 4, the lug 46 moves out of abutting relationship with the abutment surface 48 which allows the outer pusher sleeve to be moved relative to the inner tubular member 4 towards the front end of the device, thereby to push an elastic band off the front end of the device onto hemorrhoidal tissue. The locking mechanism 40 ensures that unintentional deployment of the elastic band as a result of movement of the outer pusher sleeve towards the front end of the device does not occur until the outer pusher sleeve is unlocked by the user.

Device would be supplied to end user with the lock engaged such that the band pusher would not move. User would; attach loading cone, load band and lubricate as normal. Insert device and locate tissue. Pull back on plunger until lock ring is engaged, oscillate to confirm bite of material is correct. (lock feature would not prevent band pusher from oscillating freely relative to the ligator main body) Slight pressure would be applied to the band pusher thumb flange, the angle of the thumb flange would cause the release of the teeth engaged/locked. Band pusher proceeds forward to release and deploy the band. Band pusher can be pulled back to re-engage the mechanism (to keep contaminated device together) Plunger pushes forward to release material and device is removed.

Final amount of engagement needs to be determined, when engaged a static load of 2 lbs would be desirable. Final angle of thumb flange to clear engagement needs to be determined. An audible click would be desirable to confirm engagement however dis-engagement would however be preferably near silent.

Figure 2B:
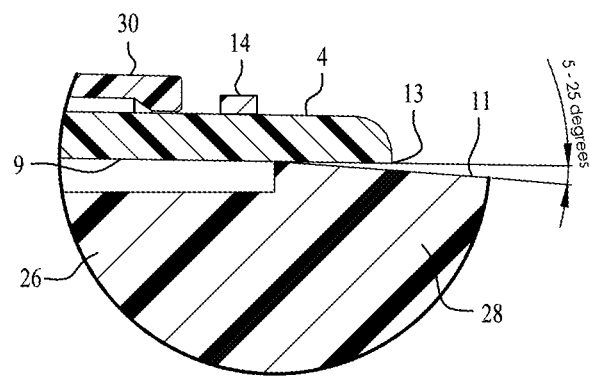
FIG. 2B is a cross-sectional view of the end of the device showing the end of the obturator partially protruding from the end of the device.

FIG. 2B shows in cross-section the distal end of the inner tubular member end 4 with the end 28 of the obturator partially protruding from the opening 13. The outer surface 11 of the end 28 is convergent towards the distal tip of the obturator, creating an angle of 5-25 degrees between the outer surface 11 of the obturator end 28 and the inner surface 9 of the inner tubular member 4. This feature serves to reduce pinching of tissue when the obturator 26 is moved relative to the inner tubular member, particularly when the obturator is withdrawn into the inner tubular member 4. This anti-pinch feature allows gaps to increase as components move together, or allows for no gap as they move together, thereby minimizing the risk of pinching of tissue as the end of the obturator emerges from or is retracted into the inner tubular member 4. In the illustrated arrangement, pinching is reduced as the pinch area increases allowing material to move away freely. As indicated in FIG. 2B, the angle between the outer surface of the end 28 and the inner surface of the inner tubular member is typically in the range of 5-25 degrees, for example 5-10 degrees, and is typically about 30 degrees or less.

Figure 3A:
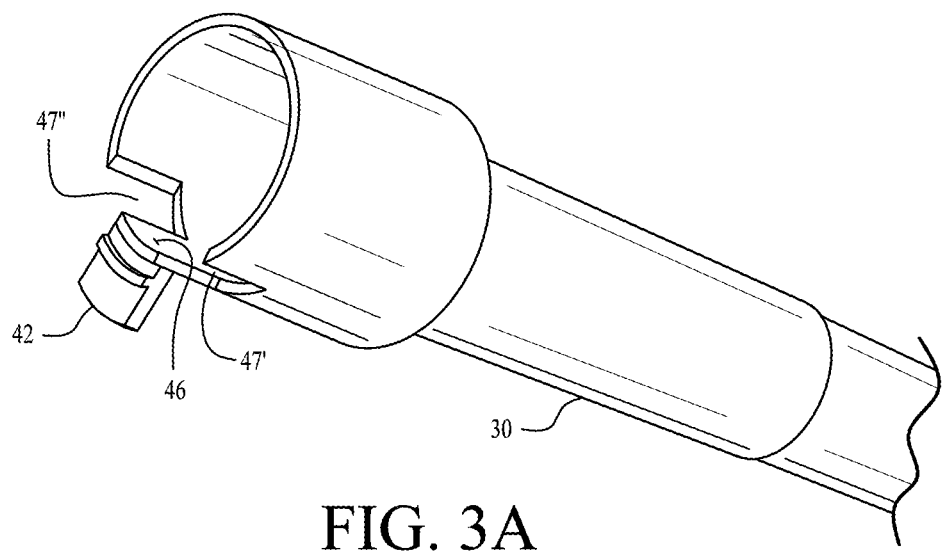
FIG. 3A is a perspective view of the outer pusher sleeve showing the tab of the locking mechanism and an enlarged inset view thereof.

FIG. 3A shows the tab 42 and the lug 46. Cut-outs 47' and 47" are provided to permit adjustment to tune the force required to deflect the tab 42 away from the inner tubular member. The highest force would be a configuration with no cut-out, decreasing in force as the cut-outs deepen and widen.

FIG. 3B is a side view of the outer pusher sleeve 30 and FIG. 3C is a top view of the outer pusher sleeve 30. FIG. 3D is a cross-sectional view of the outer pusher sleeve 30 along the line 3D-3D in FIG. 3C and FIG. 3E is a view from the distal end of the outer pusher sleeve 30. FIG. 3F is a view from the proximal end of the outer pusher sleeve 30.

FIG. 4 shows the inner tubular member 4 with the locking ring 44 disposed on the outer circumference thereof. The shape of the locking ring is shown in greater detail in FIG. 2A.

Figure 5A:
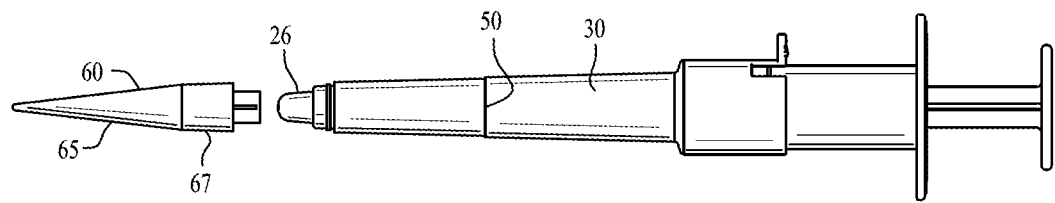
FIG. 5A is a side view of an embodiment of the ligation device of the invention showing the obturator extending from the end of the inner tubular member and the outer pusher sleeve locking mechanism engaged with the locking ring on the outer circumference of the inner tubular member (an elastic band introducer is also shown adjacent the distal end of the device)
Figure 5B:
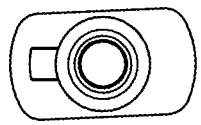
FIG. 5B is a view from the distal end of the device shown in FIG. 5A.

FIG. 5A shows a circumferential ring marker 50 provided on the external circumference of the outer tubular pusher sleeve 30. This serves as a depth marker to the user with regard to the extent of insertion of the device into the rectum of the patient. FIG. 5A also shows the obturator 26 protruding from the end of the inner tubular member. FIG. 5B is a view from the distal end of the device shown in FIG. 5A.

Figure 6A:
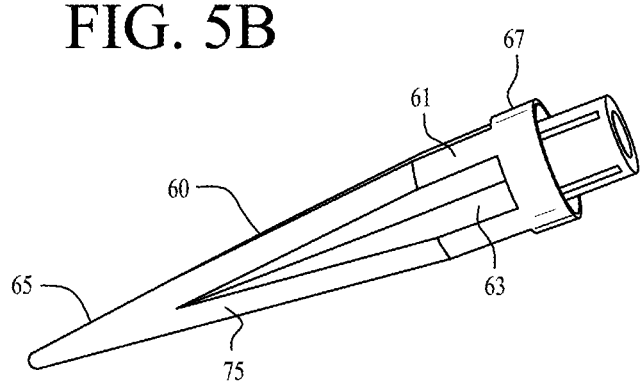
FIG. 6A is perspective view of the elastic band introducer showing surface ribs and channels.
Figure 6B:
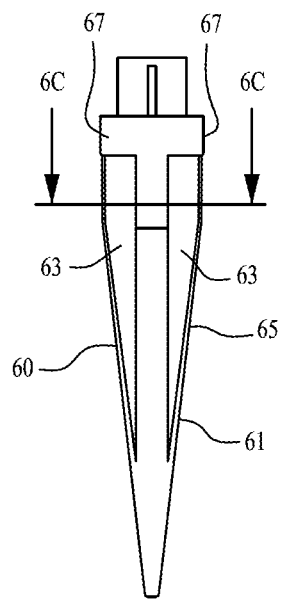
FIG. 6B is a side view of the elastic band introducer of FIG. 6A.
Figure 6C:
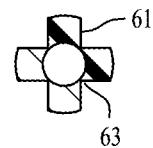
FIG. 6C is a cross-sectional view of the elastic band introducer along the line 6C-6C in FIG. 6B.

FIGS. 6A-6C show views of the elastic band introducer 60. FIG. 6A is perspective view of the elastic band introducer 60 showing surface ribs 61 and channels 63. FIG. 6B is a side view of the elastic band introducer of FIG. 6A and FIG. 6C is a cross-sectional view of the elastic band introducer along the line 6C-6C in FIG. 6B. The tapered surface 65 of the introducer 60 facilitates loading of elastic bands thereon by rolling the bands onto flat region 67 of the introducer prior to pushing the bands onto the inner tubular member 4.

Figure 7:
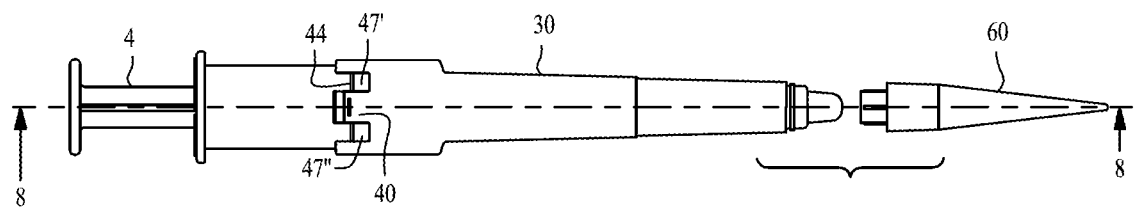
FIG. 7 is an side view of the device showing the locking mechanism on the outer pusher sleeve.

FIG. 7 shows a side view of the device showing the locking mechanism 40 and cut outs 47' and 47". In the embodiment shown, the locking mechanism 40 is engaged with the locking ring 44 on the inner tubular member 4.

Figure 10:
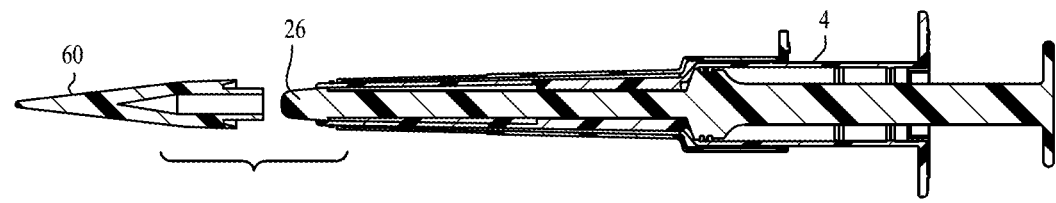
FIG. 10 is a cross-sectional view of the device showing the obturator protruding from the end of the device.

FIG. 8 is a cross-sectional view of the device showing the obturator 26 partially withdrawn inside the inner tubular member 4, and FIG. 9 is a cross-sectional view of the device showing the obturator 26 fully withdrawn inside the inner tubular member 4. FIG. 10 is a cross-sectional view of the device showing the obturator 26 protruding from the end of the inner tubular member 4.

Figure 11:
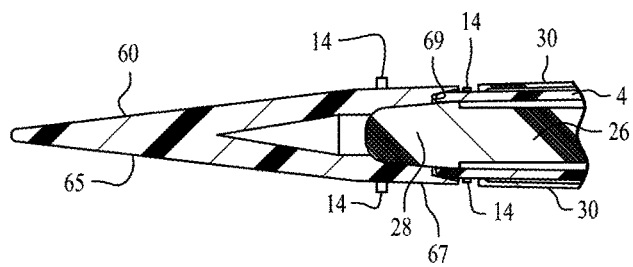
FIG. 11 is a cross-sectional view showing the elastic band introducer on the distal end of the device.

FIG. 11 is a cross-sectional view of the elastic band introducer 60 on the distal end of the inner tubular member 4 whereby the end of the inner tubular member 4 is received within slot 69 of the introducer 60. In this way, elastic band(s) 14 loaded on the flat region 67 can be rolled onto the outer surface of the inner tubular member downstream of the distal end of the outer tubular pusher sleeve 30.

Figure 12:
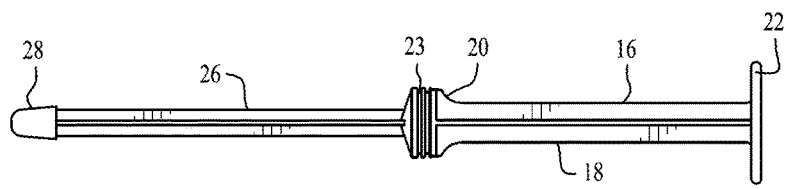
FIG. 12 is a side view of an obturator.

FIG. 12 is a side view of a combined plunger 16 and obturator 26 for use in the device of the invention. As noted earlier, the plunger and obturator may be separate items or may be integrally formed in one piece, as shown in FIG. 12. The rounded end section 28 facilitates more comfortable access of the ligation device into the rectum of a patient.

Figure 13:
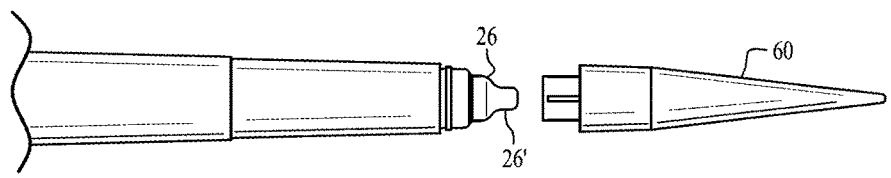
FIGS. 13 and 14 are side views of an alternative embodiment showing a differently shaped end for the obturator.
Figure 14:
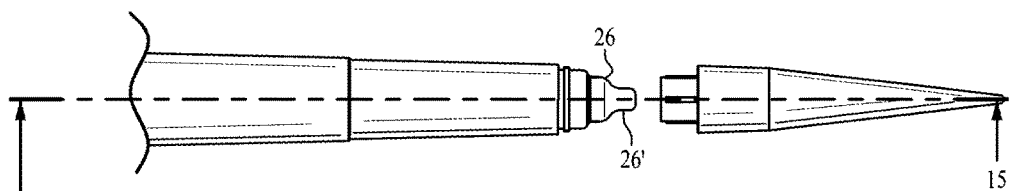

FIGS. 13 and 14 are side views of an alternative embodiment showing a differently shaped end for the obturator 26. In this embodiment, the distal end of the obturator has a region of reduced diameter 26' towards the tip to further facilitate entry of the device into the rectum of the patient and to reduce the incidence of pinching of tissue as the obturator is withdrawn into the device after deployment of a band onto the hemorrhoidal tissue.

Figure 15:
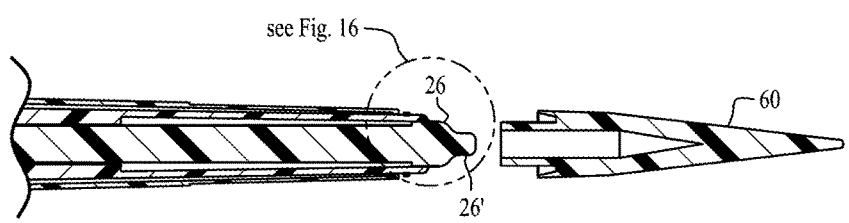
FIG. 15 is a cross-sectional view along line 15-15 of FIG. 14.

FIG. 15 is a. cross-sectional view along line 15-15 of FIG. 14. FIG. 16 is a cross-sectional view of the circled portion of FIG. 15 showing in greater detail the region 26' of reduced diameter towards the obturator tip.

FIG. 17 is a cross-sectional view of the circled portion of FIG. 16 showing an alternative embodiment whereby a flexible anti-pinch wiper element 70 suitably of a thin plastics material is connected to, or integrally formed with, the end of the inner tubular member 4. The flexible anti-pinch element 70 is disposed such it abuts against the outer surface of the end of the obturator and prevents tissue from being trapped or pinched between the outer surface of the end of the obturator and the inner surface of the inner tubular member 4.

FIGS. 18 and 19 are side views of another embodiment showing a differently shaped end for the obturator. In this embodiment, the end 72 has parallel walls 74 rounded at 76 at the tip of the obturator, which reduces the incidence of pinching of tissue.

Figure 21:
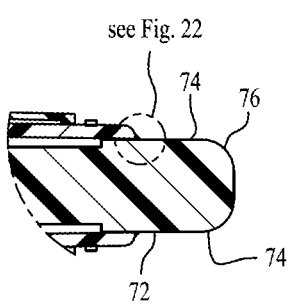
FIG. 21 is a cross-sectional view of the circled portion of FIG. 20.

FIG. 20 is a cross-sectional view along line 20-20 of FIG. 19. FIG. 21 is a cross-sectional view of the circled portion of FIG. 20 showing in greater detail the region the configuration of the obturator tip 72.

Figure 22:
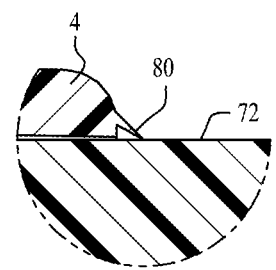
FIG. 22 is a cross-sectional view of the circled portion of FIG. 21.

FIG. 22 is a cross-sectional view of the circled portion of FIG. 21 showing a further alternative embodiment whereby a flexible anti-pinch wiper element 80 suitably of a thin plastics material is connected to, or integrally formed with, the end of the inner tubular member 4. The flexible anti-pinch element 80 is disposed such it abuts against the outer surface of the end of the obturator 72 and prevents tissue from being trapped or pinched between the outer surface of the end of the obturator 72 and the inner surface of the inner tubular member 4.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An elastic band ligation device for treatment of hemorrhoidal tissue, comprising:
    an inner tubular member having an inner surface, an outer surface, a front end and a rear end, for retaining a stretched elastic band over the front end thereof, the front end having an opening, the inner tubular member extending for a sufficient distance for insertion into a rectum of a patient;
    a plunger in the inner tubular member with a handle means extending away from the rear end of the inner tubular member, the handle means for sliding the plunger away from the front end of the inner tubular member to provide a suction for drawing hemorrhoidal tissue into the inner tubular member through the opening at the front end;
    an outer tubular pusher sleeve having an inner configuration corresponding to that of the inner tubular member to provide a limited friction fit with the outer surface of the inner tubular member, with an external end of the outer tubular pusher sleeve positionable adjacent a stretched elastic band;
    a locking mechanism provided at an opposite end of the outer tubular pusher sleeve for locking the outer pusher sleeve and the inner tubular member to prevent movement of the outer tubular pusher sleeve towards the front end of the inner tubular member, said locking mechanism comprising a tab formed in said opposite end of said outer tubular pusher sleeve, a locking ring positioned on said outer surface of said inner tubular member, said locking ring having an abutment surface which extends outwardly from the outer surface of the inner tubular member towards the tab, said tab having a lug extending transversely from the tab towards the inner tubular member and into engagement with said abutment surface to prevent movement of the outer tubular pusher sleeve towards the front end of the inner tubular member, said tab when pressed in use disengaging the outer tubular pusher sleeve from the inner tubular member and allowing the outer tubular pusher sleeve to be moved towards the front end of the inner tubular member and into contact with the elastic band to urge the elastic band away from the front end of the inner tubular member and into engagement with hemorrhoidal tissue extending through the opening in the inner tubular member;
    said outer pusher sleeve further comprising cut-outs adjacent the tab for permitting adjustment to tune a force required to deflect the tab away from the inner tubular member.

2. The elastic band ligation device according to claim 1, wherein upon pushing the tab away from the inner tubular member, the lug moves out of abutting relationship with the abutment surface which allows the outer tubular pusher sleeve to be moved relative to the inner tubular member towards the front end of the device, thereby to push an elastic band off the front end of the device onto hemorrhoidal tissue.

3. The elastic ligation device according to claim 1, wherein a circumferential ring marker is provided on an external circumference of the outer tubular pusher sleeve as a depth marker to a user with regard to an extent of insertion of the device into the rectum of the patient.

4. The elastic ligation device according to claim 1, further comprising an elastic band introducer for facilitating introduction of elastic bands onto the inner tubular member.

5. The elastic ligation device according to claim 4, wherein the elastic band introducer has a tapered region and a flat region.

6. The elastic ligation device according to claim 5, wherein the elastic band introducer has surface ribs and channels extending along the tapered region.

7. The elastic band ligation device according to claim 6, wherein the introducer has a slot in the flat region which receives the distal end of the inner tubular member.

8. The elastic band ligation device according to claim 1, further comprising an obturator disposed within the inner tubular member.

9. The elastic band ligation device according to claim 8, wherein the obturator and the plunger are integrally formed.

10. The elastic band ligation device according to claim 8, wherein an outer surface of an end of the obturator is convergent towards a distal tip of the obturator and creates an angle of 30 degrees or less between the outer surface of the obturator end and an inner surface of the inner tubular member.

11. The elastic band ligation device according to claim 10, wherein the angle is 5-25 degrees.

12. The elastic band ligation device according to claim 8, wherein a distal end of the obturator has a region of reduced diameter towards a tip to facilitate entry of the device into the rectum of the patient and to reduce pinching of tissue as the obturator is withdrawn into the device after deployment of the elastic band onto the hemorrhoidal tissue.

13. The elastic band ligation device according to claim 8, wherein a flexible anti-pinch wiper element material is connected to an end of the inner tubular member and abuts against an outer surface of an end of the obturator to prevent tissue from being trapped or pinched between the outer surface of the end of the obturator and an inner surface of the inner tubular member.

14. The elastic band ligation device according to claim 13, wherein the wiper element is flexible and is made of a thin plastics material.

15. The elastic band ligation device according to claim 1, wherein an end of the obturator has parallel walls rounded at a tip of the obturator, to reduce pinching of tissue.

* * * * *